US006020495A

United States Patent [19]
Sun et al.

[11] Patent Number: 6,020,495
[45] Date of Patent: *Feb. 1, 2000

[54] STEREOSELECTIVE METHOD FOR SYNTHESIZING DOLAPHENINE

[75] Inventors: Xiaoyong Sun, Acton; Yesh P. Sachdeva, Concord; Donna Kaye Wilson, Billerica; Richard L. Gabriel, Swampscott; Siya Ram, Winchester, all of Mass.

[73] Assignee: Pharm-Eco Laboratories, Inc., Lexington, Mass.

[ * ] Notice: This patent is subject to a terminal disclaimer.

[21] Appl. No.: 08/986,834

[22] Filed: Dec. 8, 1997

Related U.S. Application Data

[63] Continuation of application No. PCT/US96/09140, Jun. 6, 1996, which is a continuation-in-part of application No. 08/467,013, Jun. 6, 1995, abandoned.

[51] Int. Cl.[7] .................................................. C07D 277/20
[52] U.S. Cl. .......................................... 548/202; 548/204
[58] Field of Search ..................................... 548/202, 204

[56] References Cited

U.S. PATENT DOCUMENTS

| | | | |
|---|---|---|---|
| 4,978,744 | 12/1990 | Pettit et al. | 530/330 |
| 5,200,561 | 4/1993 | Konya et al. | 564/373 |

FOREIGN PATENT DOCUMENTS

| | | |
|---|---|---|
| 0 237 305 | 9/1987 | European Pat. Off. . |
| 0 485 069 A1 | 5/1992 | European Pat. Off. . |
| 05279311 | 10/1993 | Japan . |
| 06340674 | 12/1994 | Japan . |

OTHER PUBLICATIONS

Pettit, G. R., et al., "The Absolute Configuration and Synthesis of Natural (–)–Dolastatin 10," *J. Am. Chem. Soc.*, 111: 5463–5465 (1989).

Irako, N., et al., "A New Efficient Synthesis of (S)–Dolaphenine ((S)–2–Phenyl–1–(2–thiazolyl)ethylamine), the C–Terminal Unit of Dolastatin 10," *Tetrahedron*, 48(35): 7251–7264 (1992).

Shioiri, T., et al., "Stereoselective Synthesis of Dolastatin 10 and Its Congeners," *Tetrahedron*, 49(9): 1913–1924 (1993).

Pettit, G. R., et al., "Structure of the Cyclic Peptide Dolastatin 3 from *Dolabella auricularia*," *J. Am. Chem. Soc.*, 104(3): 905–907 (1982).

Brendenkamp, M. W., et al., "Observations of the Hantzsch Reaction: Synthesis of N–[t]BOC–S–Dolaphenine," *Synthetic Communications*, 22(21): 3029–3039 (1992).

Fujita, M., et al., "Reduction of Oximes with Hydrosilame/ H[+] Reagent," *Chemistry Letters*, pp. 837–838 (1986).

Hamada, Y., et al., "New Methods and Reagents in Organic Synthesis. 67. A General Synthesis of Derivatives of Optically Pure 2–(1–Aminoalkyl)thiazole–4–carboxylic Acids," *J. Org. Chem.*, 52: 1252–1255 (1987).

Pettit, G.R., et al., "The Dolastatins 16, Synthesis of Dolaphenine," *Heterocycles*, 39(1): 81–100 (1994).

Brown, H.C. and Krishnamurthy, S., "Boranes for Organic Reductions—A Forty Year Odyssey," *Aldrichimica Acta*, 12(1): 167–175 (1979).

S. Itsuno, et al., "Asymmetric Synthesis Using Chirally Modified Borohydrides, Part 3. Enantioselective Reduction of Ketones and Oxime Ethers with Reagents Prepared from Borane and Chiral Amino Alcohols," *J. Chem. Soc. Perkin Trans.*, 1: 2039–2044 (1985).

Y. Komeyoshi, "Chiral Hydroxyphenethylamine Complexes with Borane Derivatives," *Chemical Abstracts*, 105: 114714c 642–643 (1986).

Sakito, Y., et al., "Asymmetric Reduction of Oxime Ethers. Distinction of Anti and Syn Isomers Leading to Enantiomeric Amines," *Tetrahedron Letters*, 29(2): 223–224 (1988).

Dondoni, A. and Merino, P., "Chemistry of the Enolates of 2–Acetylthiazole: Aldol Reactions with Chiral Aldehydes to Give 3–Deoxy Aldos–2–uloses and 3–Deoxy 2–Ulosonic Acids. A Short Total Synthesis of 3–Deoxy–D–manno–2–octulosonic Acid (KDO)," *J. Org. Chem.*, 56: 5294–5301 (1991).

Welch, W.M., et al., "Nontricyclic Antidepressant Agents Derived from cis– and trans–1–Amino–4–aryltetralins," *J. Med. Chem.*, 27: 1508–1515 (1984).

Noyori, R., et al., "Rational Designing of Efficient Chiral Reducing Agents. Highly Enantioselective Reduction of Aromatic Ketones by Binaphthol–Modified Lithium Aluminum Hydride Reagents," *J. Am. Chem. Soc.*, 106: 6709–6716 (1984).

Bøgesø, K.P., et al., "3–Phenyl–1–indanamines. Potential Antidepressant Activity and Potent Inhibition of Dopamine, Norepinephrine, and Serotonin Uptake," *J. Med. Chem.*, 28: 1817–1828 (1985).

Schmidt, U., et al., "Synthesis of Optically Active 2–(1OHydroxyalkyl)–thiazole–4–carboxylic Acids and 2–(1–Aminoalkyl)–thiazole–4–carboxylic Acids," *Synthesis*, pp. 992–998 (Dec. 1986).

Sakane, H., et al., "Preparation of dimethoxydeoxybenzoin oxime derivatives as intermediates for optically active 1,2–bis(4–methoxyphenyl)ethylamine," (from *Chemical Abstracts*, 1994, 120, Abstract No. 191318). (This abstract corresponds to reference AN, Japanese Patent No. 05,279, 311).

(List continued on next page.)

*Primary Examiner*—Robert Gerstl
*Attorney, Agent, or Firm*—Hamilton, Brook, Smith & Reynolds, P.C.

[57] ABSTRACT

The present invention relates to a method for the stereospecific synthesis of an enantiomer of a chiral amine, wherein the chiral amine has the formula $R^1CH(NH_2)R^2$. $R^1$ and $R^2$ are each independently selected from the group consisting of alkyl, aryl and heterocyclic and radicals. This method is particularly useful for stereospecifically synthesizing S-dolaphenine. The method involves contacting a chiral enantiomer of norephedrine with borane, within an aprotic solvent to form a complex for stereospecifically reducing oximes. The complex is then contacted with an oxime, thereby stereospecifically reducing said oxime to form an enantiomer of a chiral amine.

25 Claims, No Drawings

OTHER PUBLICATIONS

Sakane, H. and Suzukamo, T., "Preparation of optically active oxazaborolidines as asymmetric reducing agents," (from *Chemical Abstracts*, 1995, 123, Abstract No. 56272). (This abstract corresponds to reference AN, Japanese Patent No. 06,340,674).

Janot, et al., "(3α,5α)-3-Aminopregnan-20-one; 3α-amino-20-oxo-5α-pregnane," *Compt. Rend.*, 246: 3076(1958). (From The Merck Index, 12th Ed., 1996, Abstract No. 4314. Funtumine.).

Fouche, J.C. and Gueremy, C.G.A., "10,11-Dihydro-N,5-dimetyl-5H-dibenz[b,flazepin-10-amine; 10,11-dihydro-5-methyl-10-(methylamino)-5H-dibenz[b,flazepine," S. Afr. pat. 68 00345 corresp to U.S. pat. 3,622,565 (1968/1971). (From The Merck Index, 12th Ed., 1996, Abstract No. 5991. Metapramine.).

STEREOSELECTIVE METHOD FOR SYNTHESIZING DOLAPHENINE

RELATED APPLICATION

This application is a Continuation of PCT/US96/09140 filed on Jun. 6, 1996, which is a Continuation-in-Part application of U.S. Ser. No. 08/467,013 filed with the United States Patent and Trademark Office on Jun. 6, 1995 now abandoned, the entire teachings of which are hereby incorporated into this application by reference.

GOVERNMENT FUNDING

This invention was made with Government support under Contract No. NO1-CM-27764 awarded by the National Institute of Health. The Government has certain rights in the invention.

BACKGROUND OF THE INVENTION

Dolastatin 10 is a highly potent antineoplastic peptide chain of S-dovaline at the C-terminus, S-valine, (3R, 4S, 5S)-dolaisoleuine, (2S,2'R,3'R)-dolaproine and S-dolastatin at the N-terminus. Dolastatin 10 was originally isolated from the Indian Ocean sea hare *Dolabella auricularia*. However, sufficient amounts of Dolastatin 10 cannot reasonably be obtained from *Dolabella a*. Consequently, to support commercial production of Dolastatin 10, various methods have been developed to synthesize the C-terminus unit, S-dolaphenine. However, these methods for synthesizing S-dolaphenine typically require many synthetic steps, often resulting in reduced product yields and/or racemic mixtures of R- and S-dolaphenine.

Therefore, a need exists for a simpler method of stereoselectively forming S-dolaphenine with higher product yields.

SUMMARY OF THE INVENTION

The present invention relates to a method of stereoselectively forming at least one enantiomer of a chiral amine, wherein the chiral amine has the formula $R^1CH(NH_2)(R^2)$. $R^1$ and $R^2$ are each independently selected from the group consisting of lower alkyls, aryl and heterocyclic radicals. This method is particularly useful for stereoselectively synthesizing S-dolaphenine. The method involves contacting at least one diastereomer of norephedrine with borane, wherein the borane is complexed with an aprotic solvent, to form a norephedrine complex for stereoselectively reducing oximes. The norephedrine complex is then contacted with an oxime, having the formula $R^1C(=NOR^3)R^2$ wherein $R^3$ is an alkyl or aryl radical, within an aprotic solvent to stereoselectively reducing said oxime to form at least one enantiomer of a chiral amine.

This invention has the advantage of providing an economical, simpler method of forming relatively pure enantiomers of chiral amines, such as S-dolaphenine in higher yields.

DETAILED DESCRIPTION OF THE INVENTION

The terms stereoselective, stereoisomer, chiral and enantiomer are as classically defined in the art. For instance, stereoisomers are configurational isomers that are different from each other only in the way the atoms are oriented in space, but are like one another with respect to which atoms are joined to which other atoms. Stereoisomers which are not superimposable upon their mirror images are chiral. Further, such non-superimposable, mirror-image stereoisomers are enantiomers.

Enantiomers are distinguishable by optical activity and configuration. An amine having the formula $R^1CH(NH_2)(R^2)$, wherein the amine is chiral (thus $R^1$ is not the same as $R^2$) has two enantiomers having different configurations about the chiral center (the carbon of the CH group), the R-configured isomer and the S-configured isomer.

A lower alkyl is defined herein as a $C_1$ to $C_{10}$ branched, cyclic or straight-chained aliphatic hydrocarbon, which may optionally be saturated or unsaturated, and which may optionally be substituted with an aryl and/or heterocyclic group and/or one or more times with a whole group. Examples of suitable alkyl groups include, for instance, methyl, ethyl, propyl, butyl and iso-butyl groups. A preferred substituted alkyl, of this invention, is a benzyl group.

Aryl groups of the present invention include $C_6$ to $C_{14}$ aryl radicals. An aryl group may also be optionally substituted one or more times with a $C_1$ to $C_4$ alkyl, a $C_1$ to $C_4$ alkoxy, a phenyl, a phenyloxy or a halo group. Examples of suitable aryl groups include phenyl and naphthyl groups, and of substituted aryl groups include dibenzyl, chlorophenyl and methylphenyl groups.

Further, heterocyclic radicals are defined as $C_3$ to $C_{12}$ carbon rings containing from 1 to 3 heteroatoms, such as nitrogen, oxygen and/or sulfur, within the carbon ring. A heterocyclic radical may optionally be substituted one or more times with a $C_1$ to $C_4$ alkyl group or a halo group. Suitable heterocyclic radicals include, for instance, imidazolyl, pyridyl, pyrrolyl, thiophenyl, pyrimidyl, thiazolyl and furyl groups.

The norephedrine used in this method typically comprises (1S,2R)-(+)-norephedrine, (1R,2S)-(–)-norephedrine, or mixtures thereof. It is understood that the norephedrine used can be in a solid state, or preferably dissolved in a suitable aprotic solvent, such as tetrahydrofuran (THF).

The borane used in the method of invention is in the form of borane complexed with a aprotic solvent, such as THF, pyridine, poly(2-vinyl pyridine), 1,4-oxathiane, 2,6-lutidine or 4-methylmorpholine. These complexed-boranes are commercially available from Aldrich Chemicals (Milwaukee, Wis.). The preferred complexed-borane is a borane-THF complex. An even more preferred borane-complex comprises a 1.0 M solution of borane-THF complex in THF.

Either (1S,2R)-(+)-norephedrine, or (1R,2S)-(–)-norephedrine, or a combination thereof can be contacted with complexed-borane to form a solution for stereoselectively reducing oximes. In this method, norephedrine is contacted with a complexed-borane under anhydrous conditions to form said stereoselective reducing solution.

Anhydrous conditions, as defined herein, means no water is present with the reagents or solvent and that the reaction is performed in an inert atmosphere, such as under argon or nitrogen. Preferably, no significant amount of free oxygen is present under anhydrous conditions.

Generally, from about 0.1 moles to about 10 moles, or more, of complexed-borane are used per mole of norephedrine. It is preferred to use an amount of complexed-borane in excess of 2 moles of complexed-borane per mole of norephedrine. To control the rate of energy released upon contacting complexed-borane with norephedrine, the rate of addition can be slowed, such as by dropwise addition, and/or the reaction can be performed under cold conditions, such as below 0° C. When using borane-THF complex, it is preferred to perform the reaction at a temperature of about –40° C. or less.

To stereoselectively form at least one enantiomer of the chiral amine product, the stereoselective reducing solution is contacted with an oxime, having the formula $R^1C(=NOR^3)R^2$. Typically, the stereoselective reducing solution is formed under anhydrous conditions.

The oxime used can be in a solid or liquid form or can be in solution within an aprotic solvent. Typically, from about 0.1 moles to about 1.0 moles of oxime are used per mole of norephedrine in the stereoselective reducing solution. Preferably, from about 0.3 moles to about 0.5 moles of oxime are used per mole of norephedrine.

In one embodiment of the method of this invention, a first enantiomer of said chiral amine is stereoselectively formed either by contacting the anti-oxime isomer with a first stereoselective reducing solution, formed using (1S,2R)-(+)-norephedrine, or by contacting the syn-oxime with a second stereoselective reducing solution, formed using (1R,2S)-(–)-norephedrine.

In a preferred embodiment, the first chiral amine enantiomer comprises S-dolaphenine. S-dolaphenine is stereoselectively formed according to this method by contacting anti-benzyl 2-thiazolyl ketone O-methyloxime with the first stereoselective reducing solution or alternatively, by contacting syn-benzyl 2-thiazolyl ketone O-methyloxime with the second stereoselective reducing solution. See Example 3 for further description of the synthesis of S-dolaphenine from the syn-oxime.

In another embodiment, a second enantiomer of said chiral amine can be formed by contacting either the syn-oxime with said first stereoselective reducing solution, or the anti-oxime with said second stereoselective reducing solution.

In yet another embodiment, the second chiral amine enantiomer comprises R-dolaphenine. R-dolaphenine is stereoselectively formed according to this method by contacting syn-benzyl 2-thiazolyl ketone O-methyloxime with the first stereoselective reducing solution or alternatively, by contacting anti-benzyl 2-thiazolyl ketone O-methyloxime with the second stereoselective reducing solution. See Example 5 for further description of the synthesis of R-dolaphenine from the anti-oxime.

In a further embodiment, an enantiomeric mixture of the first and the second enantiomers of the chiral amine is formed by contacting a single oxime isomer (anti- or syn-) with a third stereoselective reducing solution, formed using both (1R,2S)-(+)-norephedrine and (1S,2R)-(–)-norephedrine. Alternatively, an enantiomeric mixture is formed by contacting the first or the second stereoselective reducing solution with a mixture of the anti-oxime and the syn-oxime. Example 7 further describes forming an enantiomeric mixture of S-dolaphenine and R-dolaphenine by contacting a mixture of the syn-isomer and the anti-isomer of benzyl 2-thiazolyl ketone O-methyloxime with the first reducing solution.

In yet another embodiment, an enantiomeric mixture is formed by contacting the third stereoselective reducing solution with the anti-oxime, the syn-oxime or a mixture thereof.

Enantiomeric mixtures of different chiral amine enantiomers can then be separated by means known in the art, such as by resolution with tartaric acid. Example 8. further describes the resolution of a racemic solution of dolaphenine, with tartaric acid, into S-dolaphenine and R-dolaphenine.

In one embodiment, a protecting group, for instance tert-butoxycarbonyl ("BOC"), carbobenzyloxy ("CBZ"), or 9-fluorenylmethoxycarbonyl ("FMOC"), is substituted into the amino group of a chiral amine enantiomer by means known in the art. Examples 4 and 6 describe protecting the amino groups of S-dolaphenine and R-dolaphenine, respectively.

Examples of methods to form a suitable oxime for use in this method, include contacting a ketone ($R^1C(O)R^2$) with a hydroxylamine derivative ($R^3ONH_2$), or a salt thereof, in an aprotic solvent to form an oxime of the formula $R^1C(=NOR^3) R^2$.

In the method wherein at least one chiral enantiomer of dolaphenine is formed, the oxime used comprises at least one isomer of benzyl 2-thiazole ketone O-methyloxime. In one embodiment benzyl 2-thiazole ketone O-methyloxime is formed from benzyl 2-thiazole ketone. Specifically, benzyl 2-thiazolyl ketone (7.0 g, 31 mmol) in pyridine (40 mL), O-methylhydroxylamine hydrochloride (6.5 g, 32 mmol) was added portionwise to form a reaction mixture. The reaction mixture was stirred at room temperature for 6 hour.

Methods of forming a suitable ketone include, for example, contacting an acid chloride ($R^1C(O)Cl$) with a silyl compound ($Si(R^4)_3R^2$) within an aprotic solvent. Each $R^4$ is independently selected from lower alkyl, aryl and heterocyclic radicals.

In one embodiment, benzyl 2-thiazolyl ketone is formed from 2-trimethylsilylthiazole. To a stirred solution of 2-trimethylsilylthiazole (14.4 g, 63 mmol), dissolved in methylene chloride (40 mL) and cooled in an ice bath, phenylacetyl chloride (19.9 g, 136 mmol), dissolved in methylene chloride (40 mL), was added dropwise to form a reaction mixture. After addition, the reaction mixture was warmed to room temperature and stirred for 20 hours.

Ketoximes which include substituted thiazoles can be converted into optically active analogues of dolaphenine by the method of this invention. Dolaphenine analogues prepared by the method of this invention provide analogues of Dolastatin 10, a known antineoplastic compound. The invention provides a method to prepare optically active analogues of Dolastatin 10 which are useful in correlating structural modifications with pharmacological activity. Suitable substituents include $C_1$–$C_4$ alkyl groups or halogens.

Multicyclic groups are also suitable for use with the method of the invention. Examples include structures of structural Formula I:

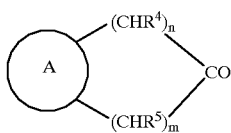

wherein each $R^4$ and each $R^5$ are independently selected from the group consisting of hydrogen, lower alkyls, substituted or unsubstituted aryls and substituted or unsubstituted heterocycles. A is selected from the group consisting of aryls, heterocycles, $C_5$–$C_8$ cycloalkyls, and fused polycyclics comprising aryls, heterocycles and/or cycloalkyls, such as, for example, the ring system characteristic of steroids. N and m are positive integers, provided that m+n≦5. A preferred structure for use in the method of the invention includes a compound represented by structural Formula I, wherein n is zero, m is 3 and A is phenyl. Another preferred structure for treatment by the method of the invention includes a compound wherein n is zero, m is 2 and A is phenyl.

The invention provides a method of preparing asymmetric amine intermediates from nonasymetric ketones as described above. The asymmetric amines can further be converted into compounds which have pharmacological properties. Examples of suitable compounds which can be transformed into optically active chiral amine compounds by the method of this invention and which can then be further transformed into pharmacologically active compounds, include, for example, the following:

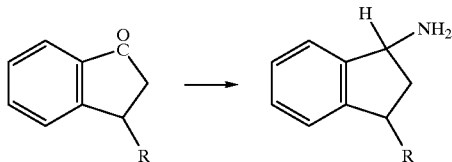

wherein R can be hydrogen, lower alkyls, substituted or unsubstituted aryls and substituted or unsubstituted heterocycles. Additionally, when R is a substituted aryl group, for example, phenyl or 2, 4-chlorophenyl, the method of the invention produces a chiral amine intermediate to 3-phenyl-1-indanamines. 3-Phenyl-1-indanamines have antidepressant activity and inhibit dopamine, norephedrine and serotonin uptake. Bogeso, K. P. et al. J. Med. Chem. 1985, 28, 1817. Also, the method of the invention can be used for stereoselectively forming chiral amines, such as aminotetralins, from alpha-tetralone derivatives as depicted below:

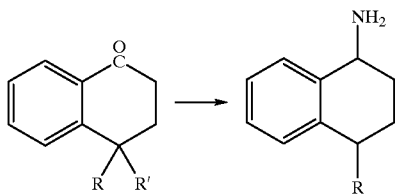

wherein R can be hydrogen, lower alkyls, substituted or unsubstituted aryls and substituted or unsubstituted heterocycles. R' can be a hydrogen or hydroxyl. When R is a substituted aryl group, such as, for example, phenyl or 2, 4-dichlorophenyl, the method of the invention produces chiral amines, such as 1-amino-4-(substituted aryl)tetralins, which have antidepressant activity and inhibit serotonin uptake. Welch, W. M. et al. J. Med Chem. 1984, 27, 1508.

The invention will now be further and specifically described by the following examples.

EXAMPLE 1

Synthesis of Benzyl 2-Thiazolyl Ketone

To a stirred solution of 2-trimethylsilylthiazole (14.4 g, 63 mmol), dissolved in methylene chloride (40 mL) and cooled in an ice bath, phenylacetyl chloride (19.9 g, 136 mmol), dissolved in methylene chloride (40 mL), was added dropwise to form a reaction mixture. After addition, the reaction mixture was warmed to room temperature and stirred for 20 hours. The reaction mixture was then quenched with saturated NaHCO$_3$ aqueous solution. The organic layer was separated and washed with 1 N NaOH solution, water, saturated aqueous NaCl, and dried over anhydrous Na$_2$SO$_4$. After filtration, concentration of the organic layer, in vacuo, gave an orange oil-like residue, which was purified by silica gel column chromatography with CH$_2$Cl$_2$/hexane (9:1, R$_f$=0.51) to give benzyl 2-thiazoly ketone (9.0 g, 50%) as a pale yellow solid, which was then recrystallized from EtOAc/hexane. mp 60.5–61.5° C.

IR (KBr):1680, 1370, 720 cm$^{-1}$. $^1$H-NMR (CDCl$_3$) δ: 4.50 (s,2H), 7.1 (m,5H), 7.54 (d,1H,J=3 Hz), 8.10 (d,1H,J=3 Hz).

EXAMPLE 2

Synthesis of Benzyl 2-Thiazolyl Ketone O-Methyloxime

To a solution of benzyl 2-thiazolyl ketone (7.0 g, 31 mmol) in pyridine (40 mL), O-methylhydroxylamine hydrochloride (6.5 g, 32 mmol) was added portionwise to form a reaction mixture. The reaction mixture was stirred at room temperature for 6 hours. The reaction mixture was then concentrated in vacuo and the residue was diluted with water (300 mL) and extracted with EtOAc (100 mL×3). The organic layers were combined and washed with saturated aqueous NaHCO$_3$ (60 mL), water (60 mL), and saturated aqueous NaCl (60 mL). The organic solution was dried over Na$_2$SO$_4$ and concentrated, in vacuo, to provide a residue, which was purified by silica gel column chromatography. Elution with CH$_2$Cl$_2$/hexane (3:7) gave the desired anti-oxime (1.0 g) as a light pale yellow oil, with the ratio of anti/syn-oxime isomer produced at 91%. R$_f$anti=0.51, R$_f$syn=0.63 [silica gel/CH$_2$Cl$_2$:hexane(9:1)].

IR(neat): 1600, 1490, 1060, 1000, 870, 710, 700 cm$^{-1}$. $^1$H-NMR of anti-oxime (CDCl$_3$) δ: 4.12 (s,3H), 4.25 (s,2H), 7.17–7.41 (m,5H), 7.49 (d,1H,J=3 Hz), 7.95 (d,1H,J=3 Hz). $^1$H-NMR of syn-oxime (CDCl$_3$) δ: 4.05 (s,3H), 4.30 (s,2H), 7.17–7.41 (m,6H), 7.65 (d,1H,J=3 Hz).

EXAMPLE 3

Synthesis of S-(+)-Dolaphenine [S-(+)-2-Phenyl-1-(2-Thiazolyl)Ethylamine]

Borane-THF complex (1.0 M solution in THF, 44 mL, 44 mmol) was added dropwise at −78° C. to a solution of (1S, 2R)-(+)-norephedrine (3.3 g, 21.5 mmol) in THF (30 mL) while maintaining an argon atmosphere to form a borane-(1S, 2R)-(+)-norephedrine complex in solution. The resulting solution was warmed to room temperature. A solution of anti-oxime (2.0 g, 8.6 mmol) in THF (20 mL) was then added dropwise. The resulting mixture was stirred at room temperature for 16 hours and refluxed for 4 hours. After the reaction mixture was cooled to room temperature, it was gradually acidified with 18% HCl (60 mL) to convert the amine to a salt such that during chromatography the amine can be separated from norephedrine, stirred at room temperature for 2 hours, and concentrated under vacuum. The residue was diluted with water and made basic with solid NaHCO$_3$ at 0° C. until the pH was 9. The mixture was extracted with EtOAc (60 mL×3). The organic layer was then dried over anhydrous Na$_2$SO$_4$. Evaporation of the solvent, under vacuum, gave an orange oil which was purified by silica gel column chromatography. Elution with EtOAc/hexane (3:7) and then with EtOAc gave S-(+)-dolaphenine as pale yellow oil (1.5 g, 60%). [a]$^{23}$=+13° (c=1, CH$_3$OH). R$_f$=0.27 (silica gel/EtOAc).

IR (neat): 1600, 1490, 1442, 720, 690 cm$^{-1}$. $^1$H-NMR (CDCl$_3$, δ: 1.70 (s,2H), 2.90 (dd,1H), 3.41 (dd,1H), 4.55 (dd,1H), 7.25 (m,6H), 7.75 (d,1H).

Elemental analysis had predicted values of C 64.67%, H 5.92% and N 13.71% and found C 64.48%, H 6.06, and N 13.52%.

EXAMPLE 4

Synthesis of N-CBZ-S-(−)-Dolaphenine

To a vigorously stirred solution of S-(+)-dolaphenine (0.12 g, 0.58 mmol) in EtOAc (6 mL) and saturated aqueous NaHCO$_3$ (1 mL), benzyl chloroformate (0.18 g, 1.0 mmol), at room temperature, was added. The reaction mixture was stirred for 3 hours. The organic layer was separated, washed with saturated aqueous NaHCO$_3$, and dried over anhydrous Na$_2$SO$_4$. After filtration and evaporation, the residue was purified by silica gel column chromatography. Elution with EtOAc/hexane (3:7) gave a white solid of N-CBZ-S-(−)-amine (0.14 g, 80%), mp 74–75.5° C. [a]$^{23}$=−20° (c=0.7, CH$_3$OH). R$_f$=0.39 [silica gel/EtOAc:hexane (7:3)].

IR (KBr):3200, 1700, 1550, 1500, 1250, 1010 cm$^{-1}$. $^1$H-NMR (CDCl$_3$) δ: 3.3 (d,2H,J=6.6 Hz), 5.09 (s,2H), 5.37 (dd, 1H,J=7.9 Hz), 5.58 (d,1H,J=7.9 Hz), 7.05 (d,1H,J=3.3 Hz), 7.19–7.26 (m,5H), 7.32 (s,5H), 7.74 (d,1H,J=3.3 Hz).

EXAMPLE 5

Synthesis of R-(−)-Dolaphenine [R-(−)-2-Phenyl-1-(2-Thiazolyl)Ethylamine]

To a solution of (1R,2S)-(−)-norephedrine (5.5 g, 36.5 mmol), in THF (80 mL), borane-THF complex (1.0 M solution in THF, 109 mL, 109 mmol) at −78° C., was added dropwise under argon atmosphere. The resulting solution was warmed to room temperature. A solution of anti-oxime (3.4 g, 14.6 mmol), in THF (40 mL), was then added dropwise. The resulting mixture was stirred at room temperature for 16 hours and refluxed for 4 hours. After cooling to room temperature, the reaction mixture was gradually acidified with 18% HCl (60 mL), stirred at room temperature for 2 hours and concentrated in vacuo. The residue was diluted with water and basified with solid NaHCO$_3$ at 0° C. until the pH was 9, and extracted with EtOAc (60 mL×3). The organic layer was dried over Na$_2$SO$_4$. Concentration, in vacuo, gave an orange oil, which was purified by silica gel column with EtOAc/hexane (3:7) first and then EtOAc. R-(−)-dolaphenine was obtained as orange oil (1.5 g, 52%). [α]$^{23}$=−13° (c=1, CH$_3$OH). R$_f$=0.27 (silica gel/EtOAc).

IR (neat):1600, 1490, 1442, 720, 690 cm$^{-1}$. $^1$H-NMR (CDCl$_3$) δ: 1.70 (s,2H), 2.90 (dd,1H), 3.41 (dd,1H), 4.55 (dd,1H), 7.25 (m,6H), 7.75 (d,1H).

Elemental analysis had predicted values C 64.67%, H 5.92% and N 13.71% and found C 64.49%, H 6.03, and N 13.48%.

EXAMPLE 6

N-Boc-R-(+)-Dolaphenine

To a vigorously stirred solution of R-(−)-dolaphenine (0.056 g, 0.27 mmol), in THF (2 mL), di-tert-butyl-dicarbonate (0.073 g, 0.33 mmol) in THF (2 mL), was added at an ice bath temperature (about 2 to 0° C.). The reaction mixture was stirred for half an hour and warmed to room temperature. The reaction mixture was then stirred at room temperature for 16 hours. The solvent was removed in a vacuum, the residue was diluted with water, and extracted with EtOAc (20 mL×2). The organic layer was dried over anhydrous Na$_2$SO$_4$. After evaporation of the solvent, the residue was purified by silica gel column (EtOAc-hexane (3:7)). The N-Boc derivative was obtained as a white solid (40 mg, 46%). [α]$^{23}$=+23° (c=1, CH$_3$OH); R$_f$=0.4 (silica/gel/EtOAc-hexane; 3:7). IR (KBr):3220, 1700, 1515, 1250, 1160, 1010 cm$^{-1}$. $^1$H NMR (CDCl$_3$) δ: 7.8 (d,1H), 7.3–7.1 (m,6H), 5.3 (m,1H), 3.3 (d,2H), 1.61 (s,1H), 1.4 (s,9H).

EXAMPLE 7

Synthesis of Racemic Dolaphenine

To a solution of (1S,2R)-(+)-norephedrine (10.3 g, 68.9 mmol), in THF (120 mL), borane-THF complex (1.0 M solution in THF (160 mL, 160 mmol) was added dropwise at −78° C. under an argon atmosphere. The resulting solution was then warmed to room temperature. A solution of anti- and syn-oxime [3:1 mixture] (6.1 g, 27.5 mmol) in THF (80 mL) was then added dropwise. The resulting mixture was stirred at room temperature for 42 hours and refluxed for 8 hours. After cooling to room temperature, the reaction mixture was gradually acidified with 18% HCl (120 mL), stirred for 2 hours, and concentrated in vacuo. The residue was diluted with water and basified with solid NaHCO$_3$ at 0° C. until pH was 9, and extracted with EtOAc (3×60 mL). The organic layer was dried over Na$_2$SO$_4$. After filtration, concentration of organic filtrate, under vacuum gave an orange oil, which was purified by silica gel column by eluting with EtOAc/hexane (3:7) first and then EtOAc. Racemic "dolaphenine" was obtained as pale yellow oil (3.3 g, 61%) which contained significant amount of S-(+)-dolaphenine. [α]$^{23}$=+7.3°.

EXAMPLE 8

Resolution of Racemic Dolaphenine with R,R-Tartaric Acid

R,R-tartaric acid (3.5 g, 23 mmol) was added to the solution of racemic dolaphenine (3.3 g, 16.2 mmol) in ethanol (20 mL). The suspension was stirred at room temperature overnight. Then 2 mL water was added to dilute the suspension. After filtration, white solid S-amine-R,R-tartrate was restirred in the 20 mL solvent of EtOH/H$_2$O (8:1) for one hour. After filtration, the white solid (4.2 g, 74%, mp=180° C.) was dried under vacuo. The resulting solid was dissolved in small amount of water and saturated aqueous NaCO$_3$ was added and stirred for half hour, extracted with EtOAc (60 mL×3). The organic layer was washed with water and dried over anhydrous Na$_2$SO$_4$. After filtration and evaporation, pure S-(+)-dolaphenine as pale-yellow oil (2.1 g, 88%) was obtained in a ratio with R-(−)-dolaphenine of about 3–4:1. [a]$^{23}$=+13° (c=1, CH$_3$OH).

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of stereoselectively forming at least one enantiomer of a chiral amine, said amine having the formula

wherein R$^1$ is a heterocyclic radical;
wherein R$^2$ is selected from the group consisting of a lower alkyl, aryl and heterocyclic radical, comprising the steps of:
  a) contacting a diastereomer of norephedrine with borane, wherein the borane is complexed with an aprotic solvent, to form a reducing solution for stereoselectively reducing stereoisomers of oximes; and
  b) contacting said steroselective reducing solution with a stereoisomer of an oxime, having the formula $R^1C(=NOR^3)R^2$ wherein $R^3$ is a lower alkyl or aryl radical, thereby stereoselectively reducing said oxime to form at least one enantiomer of said chiral amine.

2. A method of claim 1, further comprising the step of contacting a ketone, having the formula $R^1C(O)R^2$, with a hydroxylamine derivative, having the formula $R^3ONH_2$, or a salt thereof, within an aprotic solvent, whereby the ketone is converted to an oxime having the formula $R^1C(=NOR^3)R^2$.

3. A method of claim 2, further comprising the step of contacting an acid chloride, having the formula $R^1C(O)Cl$, with a silyl compound of the formula $Si(R^4)_3R^2$, within an aprotic solvent, wherein each $R^4$ is independently selected from lower alkyl, aryl and heterocyclic radicals, whereby said acid chloride and said silyl compound react to form a ketone having the formula $R^1C(O)R^2$.

4. A method of claim 3 wherein said silyl compound is 2-trimethylsilylthiazole.

5. A method of claim 2 wherein one enantiomer of a chiral amine is formed, and wherein:
   a) said norephedrine is selected from the group consisting of (1S,2R)-(+)-norephedrine and (1R,2S)-(−)-norephedrine; and
   b) said oxime is selected from the group consisting of syn-oxime and anti-oxime.

6. A method of claim 5 wherein said chiral amine comprises dolaphenine.

7. A method of claim 6 wherein:
   a) the oxime comprises (2-thiazolyl-1-phenyl ethylidene) alkoxyimine; and
   b) the enantiomer of a chiral amine comprises S-dolaphenine.

8. A method of claim 7 wherein:
   a) said norephedrine is (1S,2R)-(+)-norephedrine; and
   b) said oxime comprises anti-(2-thiazolyl-1-phenyl ethylidene) alkoxyimine.

9. A method of claim 7 wherein:
   a) said norephedrine is (1R,2S)-(−)-norephedrine; and
   b) said oxime comprises syn-(2-thiazolyl-1-phenyl ethylidene) alkoxyimine.

10. A method for the stereoselective synthesis of an enantiomer of dolaphenine, said amine having the formula, comprising the steps of:
    a) contacting a diastereomer of norephedrine with borane, wherein the borane is complexed with an aprotic solvent, to form a reducing solution for stereoselectively reducing oximes; and
    b) contacting said reducing solution with a stereoisomer of an oxime comprising (2-thiazolyl-1-phenyl ethylidene) alkoxyimine.

11. A method of claim 10 wherein the enantiomer of dolaphenine is the S-enantiomer.

12. A method of claim 11 wherein:
    a) the stereoisomer of the oxime is the anti-isomer; and
    b) the diastereomer of norephedrine is (1S,2R)-(+)-norephedrine.

13. A method of claim 11 wherein:
    a) the stereoisomer of the oxime is the syn-isomer; and
    b) the diastereomer of norephedrine is (1R,2S)-(−)-norephedrine.

14. A method of claim 11, further comprising the steps of:
    a) contacting benzyl 2-thiazole ketone with a hydroxylamine derivative, having the formula $R^3ONH_2$, or a salt thereof, wherein $R^3$ is an alkyl or aryl radical, within an aprotic solvent, whereby the benzyl 2-thiazole ketone is converted to form the syn- and anti-isomers of (2-thiazolyl-1-phenyl ethylidene) alkoxyimine; and
    b) separating said syn-isomer from said anti-isomer.

15. A method of claim 14 wherein:
    a) $R^3$ is a methyl radical; and
    b) (2-thiazolyl-1-phenyl ethylidene) alkoxyimine is (2-thiazolyl-1-phenyl ethylidene) methoxyimine.

16. A method of claim 14, further comprising the step of contacting phenylacetyl chloride with 2-trimethylsilylthiazole, within an aprotic solvent, to form benzyl-2-thiazole ketone.

17. A method for stereoselectively forming S-dolaphenine comprising the steps of:
    a) contacting phenylacetyl chloride with 2-trimethylsilylthiazole, within an aprotic solvent, to form benzyl-2-thiazole ketone;
    b) contacting the benzyl-2-thiazole ketone with methoxyamine, or a salt thereof, within an aprotic solvent, to form the syn- and anti-isomers of (2-thiazolyl-1-phenylethylidene) methoxyimine;
    c) separating said syn-isomer from said anti-isomer;
    d) contacting a suitable diastereomer of norephedrine with borane, wherein the borane is complexed with an aprotic solvent, to form a solution agent for stereospecifically reducing an oxime; and
    e) contacting at least one isomer of (2-thiazolyl-1-phenylethylidene) methoxyimine with said reducing agent solution thereby stereospecifically forming S-dolaphenine.

18. A method for the stereoselective synthesis of an enantiomer of a chiral amine, said amine having the formula

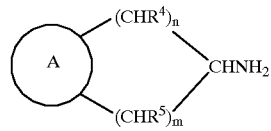

wherein A is selected from the group consisting of aryls, heterocycles, $C_5$–$C_8$ cycloalkyls and fused polycyclics comprising aryls, heterocycles and cycloalkyls;

wherein each $R^4$ and each $R^5$ is independently selected from the group consisting of hydrogen, lower alkyls, substituted or unsubstituted aryls and substituted or unsubstituted heterocycles;

wherein n is a positive integer;

wherein m is a positive integer, provided m+n≦5, comprising the steps of:
   a) contacting a diastereomer of norephedrine with borane, wherein the borane is complexed with an aprotic solvent, to form a reducing solution for stereoselectively reducing stereoisomers of oximes; and
   b) contacting said steroselective reducing solution with a stereoisomer of an oxime, having the formula

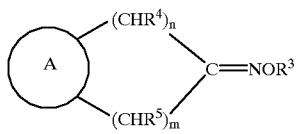

wherein A, n and m are as defined above;

wherein $R^3$ is a lower alkyl or aryl radical, thereby stereoselectively reducing said oxime to form an enantiomer of the chiral amine.

19. A method of claim 18, wherein $R^4$ and $R^5$ are hydrogen, n is 0, m is 3 and A is phenyl.

20. A method of claim 18, wherein n is 0, m is 2 and A is phenyl.

21. A method for the stereoselective synthesis of an enantiomer of a chiral amine, said amine having the formula

wherein $R^1$ is selected from the group consisting of a lower alkyl, aryl, imidazolyl, pyrrolyl, thiophenyl, pyrimidyl, thiazolyl and furyl groups and $R^2$ is a substituted or unsubstituted thiazole, comprising the steps of:
  c) contacting a diastereomer of norephedrine with borane, wherein the borane is complexed with an aprotic solvent, to form a reducing solution for stereoselectively reducing oximes; and
  d) contacting said reducing solution with a stereoisomer of an oxime, having the formula

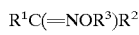

wherein $R^3$ is a lower alkyl or aryl radical, thereby stereoselectively reducing said oxime stereoisomer to form an enantiomer of the chiral amine.

22. A method for stereoselectively forming one enantiomer of an amine compound having the formula

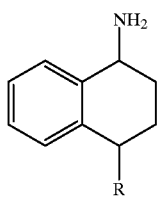

wherein:
R is selected from the group consisting of hydrogen, lower alkyls, substituted or unsubstituted aryls and substituted or unsubstituted heterocycles, comprising the steps of:
  a) contacting a diastereomer of norephedrine with borane, wherein the borane is complexed with an aprotic solvent, to form a reducing solution for stereoselectively reducing oximes; and b) contacting said reducing solution with a syn- or anti-isomer of an oxime, having the formula

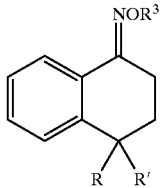

wherein:
R' is hydrogen or hydroxyl; and
$R^3$ is a lower alkyl or aryl radical, thereby stereoselectively reducing said syn- or anti-isomer of the oxime to form an enantiomer of the chiral amine.

23. A method of claim 22 wherein R is phenyl or 2,4-dichlorophenyl.

24. A method for stereoselectively forming one enantiomer of an amine compound having the formula

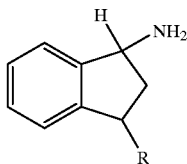

wherein R is selected from the group consisting of hydrogen, lower alkyls, substituted or unsubstituted aryls and substituted or unsubstituted heterocycles, comprising the steps of:
  a) contacting a diastereomer of norephedrine with borane, wherein the borane is complexed with an aprotic solvent, to form a reducing solution for stereoselectively reducing oximes; and
  b) contacting said reducing solution with a stereoisomer of an oxime, said oxime having the formula

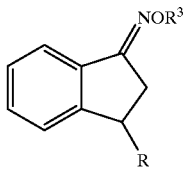

wherein $R^3$ is a lower alkyl or aryl radical, thereby stereoselectively reducing said oxime stereoisomer to form an enantiomer of the chiral amine.

25. A method of claim 24 wherein R is phenyl or 2,4-dichlorophenyl.

* * * * *